(12) United States Patent
Aymard et al.

(10) Patent No.: US 9,187,770 B2
(45) Date of Patent: Nov. 17, 2015

(54) PROCESS FOR THE PRODUCTION OF ALCOHOLS AND/OR SOLVENTS FROM LIGNOCELLULOSIC BIOMASS WITH WASHING OF THE SOLID RESIDUE OBTAINED AFTER HYDROLYSIS

(71) Applicant: IFP ENERGIES NOUVELLES, Rueil-Malmaison Cedex (FR)

(72) Inventors: Caroline Aymard, Lyons (FR); Pierre Antoine Bouillon, Bron (FR); Stephanie Fleurier, Lyons (FR); Sylvain Louret, Lyons (FR); Larissa Perotta, Lyons (FR); Eszter Toth, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 14/197,619

(22) Filed: Mar. 5, 2014

(65) Prior Publication Data

US 2014/0256012 A1   Sep. 11, 2014

(30) Foreign Application Priority Data

Mar. 6, 2013   (FR) ...................... 13 51992

(51) Int. Cl.

| | |
|---|---|
| *C12P 7/16* | (2006.01) |
| *C12P 19/14* | (2006.01) |
| *C12P 19/02* | (2006.01) |
| *C12P 1/00* | (2006.01) |
| *C12N 1/21* | (2006.01) |
| *C12M 1/00* | (2006.01) |
| *A23K 1/06* | (2006.01) |
| *A61K 35/66* | (2015.01) |
| *A61P 43/00* | (2006.01) |
| *C12P 7/10* | (2006.01) |
| *C12P 7/14* | (2006.01) |
| *C12P 7/24* | (2006.01) |
| *C12P 7/62* | (2006.01) |
| *C12P 7/06* | (2006.01) |
| *C07H 21/04* | (2006.01) |

(52) U.S. Cl.
CPC ... *C12P 7/14* (2013.01); *C12P 7/10* (2013.01); *C12P 19/14* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| | | | | |
|---|---|---|---|---|
| 4,237,226 | A | * | 12/1980 | Grethlein .................... 435/99 |
| 8,318,461 | B2 | | 11/2012 | Tolan et al. |
| 2002/0197686 | A1 | | 12/2002 | Lightner |
| 2009/0209009 | A1 | | 8/2009 | Tolan et al. |
| 2013/0022958 | A1 | | 1/2013 | Alriksson et al. |

FOREIGN PATENT DOCUMENTS

| | | |
|---|---|---|
| EP | 2336343 A1 | 6/2011 |
| WO | 83/01627 A1 | 5/1983 |
| WO | 2007/147264 A1 | 12/2007 |

OTHER PUBLICATIONS

Tom Volk's Fungus of the Month for Feb. 2000. http://botit.botany.wisc.edu/toms_fungi/feb2000.html. Down loaded Feb. 8, 2015.*
Sun et al (2005. Dilute acid pretreatment of rye straw and bermudagrass for ethanol production. Bioresource Technology, vol. 96, pp. 1599-1606).*
Malherbe et al (2002. Lignocellulose biodegradation: Fundamentals and applications. Reviews in Environmental Science & Bio/Technology, vol. 1, pp. 105-114.*
Fortman, (2009. "Techno-economic comparison of hot water and dilute acid pretreatment for biochemical production of ethanol from corn stover and evaluation of alternative scenarios to purchasing cellulase enzymes".Graduate Theses and Dissertations. Paper 10495. Iowa State University, 95 Pages.*
Search Report dated Nov. 25, 2013 issued in corresponding FR 1351992 application (pp. 1-2).
C. Liu et al., "Continuous Fermentation of Hemicellulose Sugars and Cellulose to Ethanol", XP055090067—Internet URL:http://www.eri.ucr.edu/ISAFXVCD/ISAFXVPP/CtFHSCE.pdfPresented Sep. 27, 2005.

* cited by examiner

*Primary Examiner* — Debbie K Ware
*Assistant Examiner* — Kailash C Srivastava
(74) *Attorney, Agent, or Firm* — Millen, Whie, Zelano & Branigan, P.C.

(57) ABSTRACT

The process for the production of alcohol and/or solvent from a biomass feedstock comprises the stages for pretreatment (P) of the biomass feedstock, for enzymatic hydrolysis (H) of the pretreated substrate, and for fermenting the hydrolyzate (F). To reduce the size of the fermenters, at least a portion of the solid residue contained in the hydrolyzate is extracted (Ex1) in such a way as to obtain a stream of solid residue (9) comprising lignin and a hydrolyzate (8) that is low in solid residue. Then, the stream of solid residue is washed (L) with a liquid stream in such a way as to recover a sugar-enriched liquid stream (15). The sugar-enriched liquid stream (15) is recycled in the enzymatic hydrolysis stage (H) to be able to upgrade the sugars without providing dilution of the streams in the process.

15 Claims, 3 Drawing Sheets

Figure 1:
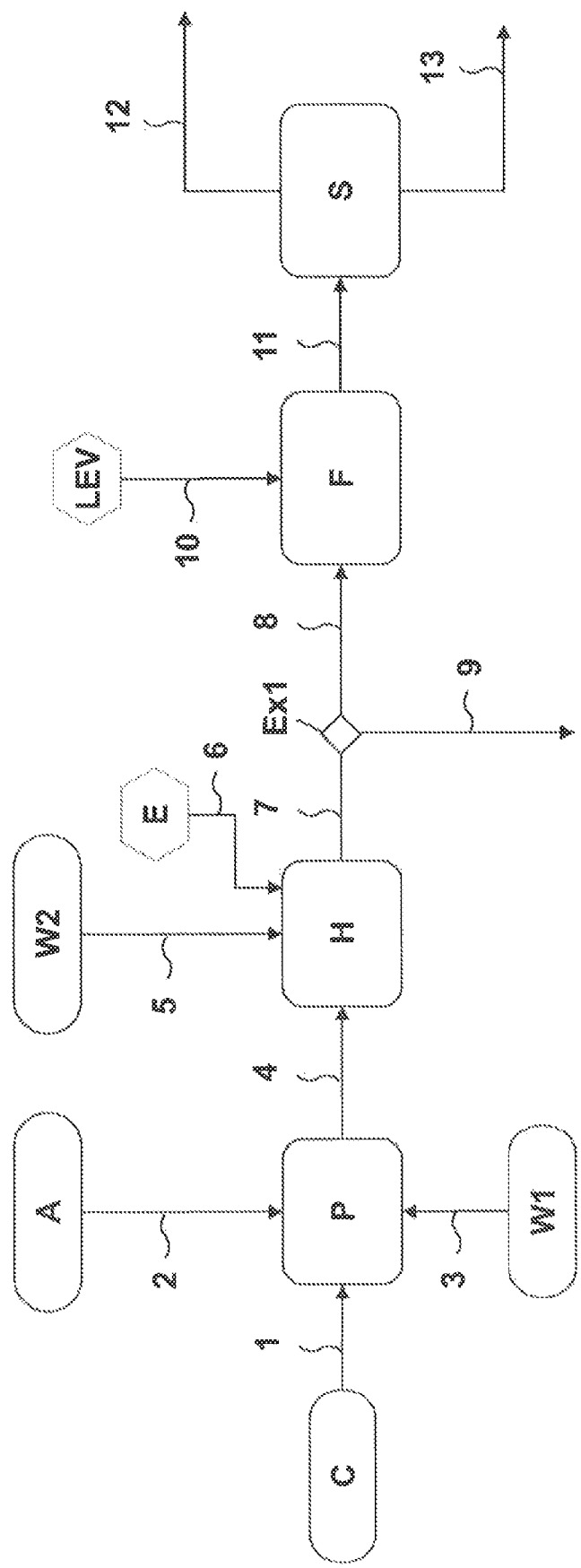

PROCESS FOR THE PRODUCTION OF ALCOHOLS AND/OR SOLVENTS FROM LIGNOCELLULOSIC BIOMASS WITH WASHING OF THE SOLID RESIDUE OBTAINED AFTER HYDROLYSIS

This invention is part of the framework of a process for the production of so-called "second-generation" alcohols and/or solvents from lignocellulosic biomass. It relates more particularly to a process for the production of ethanol and/or solvents.

The lignocellulosic biomass represents one of the must abundant renewable resources on earth. The substrates being considered are very varied since they relate at the same time to ligneous substrates (leafy and resinous), the by-products of agriculture (straw), or those of the industries that generate lignocellulosic waste (farm-produce industries, paper mills).

The lignocellulosic biomass consists of three primary polymers: cellulose (35 to 50%), which is a polysaccharide that essentially consists of hexoses; hemicellulose (20 to 30%), which is a polysaccharide that essentially consists of pentoses; and lignin (15 to 25%), which is a polymer with a complex structure and high molecular weight, composed of aromatic alcohols connected by ether bonds. These different molecules are responsible for the inherent properties of the plant wall and are organized in a complex intertwining.

The process for biochemical transformation of the lignocellulosic materials into ethanol in general comprises a stage for physico-chemical pretreatment, followed by a stage for enzymatic hydrolysis using an enzymatic cocktail, a stage for ethanolic fermentation of released sugars, and a stage for purification of the fermentation products. An example is provided by the document "Ethanol from Lignocellulosics: A Review of the Economy," M. von Silvers and G. Zacchi, Bioresource Technology 56 (1996) 131-140.

Among the three base polymers that comprise the lignocellulosic biomass, the cellulose and the hemicellulose are those that can most easily be upgraded into fermentation products. The lignin remains inert in the largest part of the processes. This is why it is advantageous for the processes for the production of alcohols and/or solvents to separate the lignin from the reaction mixtures as soon as possible so as to reduce the size of the units and the costs of treatment and investment. The lignin can be separated at different stages of the process, for example in the pretreatment, between the stages for enzymatic hydrolysis and fermentation or in the stage for purification of the fermentation products.

The document "Fuel Ethanol Production: Process Design Trends and Integration Opportunities," C. A. Cardona and O. J. Sanchez, Bioresource Technology 98 (2007) 2415-2457, describes a process where the lignin is solubilized in the presence of a solvent that makes it possible to separate the lignin from the cellulose and the hemicellulose, with the lignin next being precipitated during the pretreatment of the biomass. This solution prevents the presence of inert solids in the process starting from the enzymatic hydrolysis stage, but it has high operating costs. In addition, this configuration of the process does not promote a possible co-fermentation of the cellulosic and hemicellulosic sugars recovered in the pretreatment, considering that two streams having distinct properties and compositions are obtained.

Certain processes ("Ethanol from Lignocellulosic Biomass: Technology, Economics, and Opportunities," C. E. Wyman, Bioresource Technology 50 (1994) 3-16) call for the separation of the lignin only in the phase for purification of the products coming from the fermentation stage. This generates additional investments, in particular for the fermentation reactors that are to be sized to contain the inert lignin in addition to the reaction mixture and for the separation section that is to carry out the separation between the fermentation products and the lignin, in the case where a distillation in the presence of solids is considered.

The majority of the processes separate the lignin from other products between the stages for enzymatic hydrolysis and fermentation. However, this separation is generally carried out by tools for physical separation, which exhibit the disadvantage that the recovered inert solids can also contain trapped hydrolysis products. In this case, it is possible to add a stage for washing the solids to the process, with the effluent from this washing stage being sent to the fermentation stage with the liquid stream. This represents a compromise between the recovery of sugars and the limitations provided by the energy penalty linked to the dilution of the must to be fermented. The document "A Techno-economical Comparison of Three Processes for the Production of Ethanol from Pine," M. von Silvers and G. Zacchi, Bioresource Technology 51 (1995) 46-52, describes the impact of the washing of the recovered solid in terms of cost of the fermentation equipment, as well as a drop in the ethanol titer obtained at the end of fermentation.

This invention proposes carrying out the separation of lignin and other optional inert solids between the stages for enzymatic hydrolysis and fermentation. This solid that consists primarily of lignin is next subjected to a washing cycle for recovering the trapped hydrolysis products, in particular the sugars. The washing liquid is next recycled in the enzymatic hydrolysis unit so as not to provide dilution to the existing streams.

In a general manner, the invention relates to a process for the production of alcohol and/or solvent from a biomass feedstock, in which the following stages are carried out:

a) A pretreatment stage is carried out by heating and bringing into contact the biomass feedstock with water and an acid or basic compound in such a way as to obtain a pretreated substrate, b) The pretreated substrate is brought into contact with at least cellulase enzymes and with a liquid washing stream obtained in stage d) in such a way as to obtain a hydrolyzate comprising a solid material and a liquid phase containing sugars, c) At least a portion of the solid material contained in the hydrolyzate is extracted in such a way as to obtain a hydrolyzate that is low in solid material and a stream that is enriched with solid material, d) The stream that is enriched with solid material is washed with a liquid stream in such a way as to obtain said liquid washing stream, with the liquid washing stream being recycled in stage b), e) An alcoholic fermentation of the hydrolyzate that is low in solid material obtained in stage c) is carried out by means of an alcohologenic microorganism in such a way as to produce a fermentation wine, f) A stage for separation of the fermentation wine is carried out in such a way as to obtain at least one purified stream comprising an alcohol or a solvent and at least one vinasse stream.

According to the invention, the liquid stream from stage d) can consist of fresh water. As an alternative, the liquid stream from stage d) can comprise at least a portion of the vinasse stream obtained in stage f).

In stage b), the liquid washing stream can have a flow rate of between 50% and 1,500% by weight of the flow rate of pretreated substrate.

Before carrying out stage b), the liquid washing stream obtained in stage d) can be subjected to a second alcoholic fermentation stage by means of an alcohologenic organism.

It is possible to carry out the second alcohologenic fermentation stage under operating conditions that are different from the operating conditions of the alcohologenic fermentation of stage e). It is also possible to carry out the second alcohologenic fermentation stage with an alcohologenic organism that is different from the alcohologenic organism of the alcohologenic fermentation of stage a).

In stage d), it is possible to bring the stream that is enriched with solid material into contact with a liquid stream, and then it is possible to separate the liquid stream from the solid material.

It is possible to carry out stage d) in such a way that said stream that is enriched with solid material comprises between 15% by weight and 55% by weight of solid material and in such a way that said hydrolyzate that is low in solid material comprises less than 15% by weight of solid material.

The cellulase and/or hemicellulase enzymes can be produced by a microorganism that is selected from among the mushrooms that belong to the genera *Trichoderma, Aspergillus, Penicillium*, or *Schizophyllum*, or the anaerobic bacteria that belong to the genus *Clostridium*.

Process according to one of the preceding claims, in which the alcohologenic microorganism is selected from among the microorganisms of the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilis, Zymomonas mobilis, Clostridium, Escherichia coli*.

The biomass feedstock can consist of at least one of the following elements: wood, cultivated plants, agricultural lignocellulosic waste, residues of the industry for transformation of the lignocellulosic materials.

In stage a), it is possible to carry out a vapor explosion of the biomass by exerting compression and then by carrying out pressure relief of the biomass mixed with water and an acid compound.

In stage e), an alcohologenic organism that produces at least ethanol is used.

Figure 2:
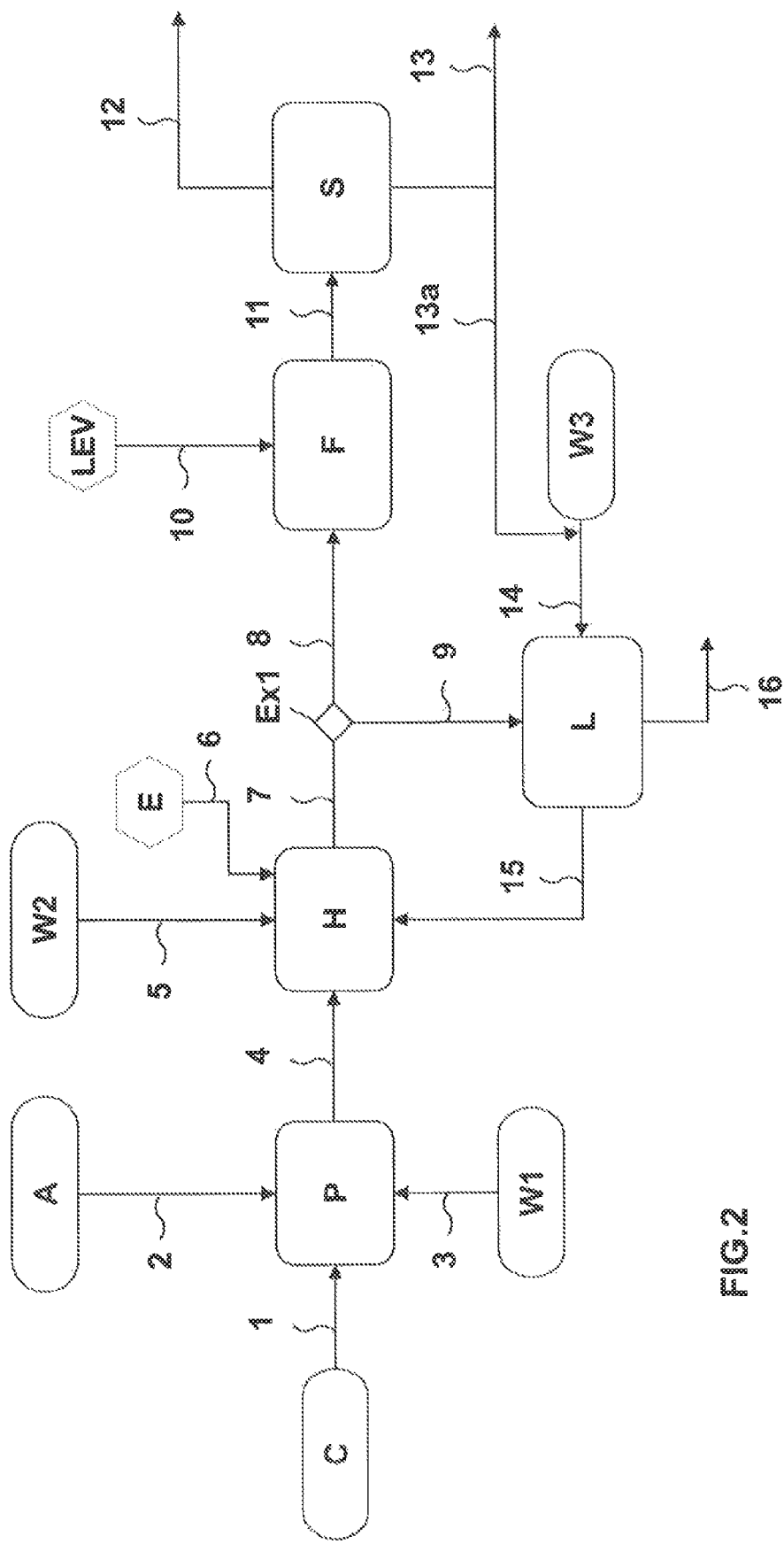
Figure 3:
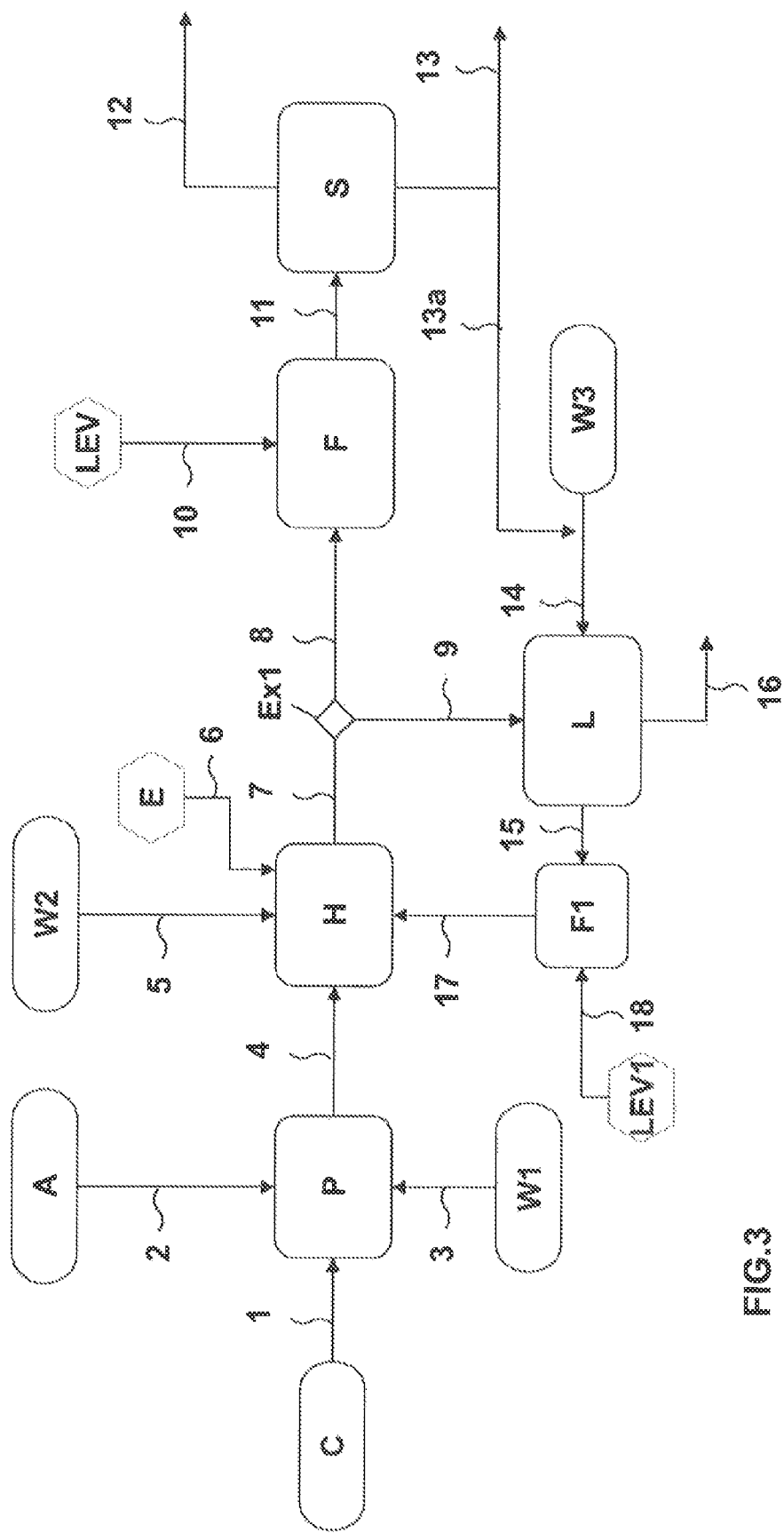

Other characteristics and advantages of the invention will be better understood and will appear clearly from reading the description given below by referring to the drawings among which:

FIG. 1 is a diagrammatic depiction of an embodiment that is not in accordance with the invention, FIG. 2 is a diagrammatic depiction of a first embodiment of the process according to the invention, FIG. 3 is a diagrammatic depiction of a second embodiment of the process according to the invention.

In terms of this invention, the solid and soluble compounds contained in a stream are referred to by the term "dry material," and the level of dry material of a stream is determined according to the ASTM E1756-01 method, which consists of a loss of mass at 105° C. The solid compounds that are present in a stream, with these solid compounds being insoluble in the liquid phase, are referred to by the term "solid material." The solid material can consist of lignin, hemicellulose and/or cellulose. The level of solid material contained in a stream can be determined by successive washing cycles of the stream with water and the analysis of the content of residual dry material of the washed stream.

With reference to FIG. 1, a biomass feedstock C is brought into the pretreatment unit P by means of the pipe 1. The biomass feedstock can consist of wood, straw, or corn stalks, products of dedicated forestry crops (for example resinous crops such as spruce or pine or leafy crops such as eucalyptus), plants of dedicated crops such as Miscanthus or switchgrass, residues of alcohologenic plants, sugar-producing plants (for example sugar cane or beets) and grains (for example, corn, wheat, . . . ), products and residues of the papermaking industry, and products for transformation of lignocellulosic materials. The feedstock can consist of approximately 35 to 50% by weight of cellulose, 20 to 30% by weight of hemicellulose, and 15 to 25% by weight of lignin.

The necessary acid or basic compound A and water W1 are respectively brought into the pretreatment unit P by means of the pipes 2 and 3 so as to carry out therein a hydrolysis reaction in an acid or basic medium. In the unit P, the biomass feedstock C is brought into contact and mixed with water W1 and the compound A in a reactor. The pretreatment unit P can carry out a mechanical action, created, for example, by means of a two-screw-type extruder or a defibering unit.

Among the acid compounds, the compound A can be selected from among sulfuric acid, hydrochloric acid, nitric acid, acetic acid, or formic acid. Among the basic compounds, the compound A can be selected from among potassium hydroxide, sodium hydroxide, and ammonia.

During the pretreatment stage in the unit P, at least one stage for heating the mixture of biomass C, water W1, and the compound A is carried out in a reactor. The water W1 can be introduced in vapor form. The pretreatment role is to make the cellulose accessible to enzymes by destructuring the lignocellulosic matrix. During pretreatment, preferably the hemicellulose is attacked, which for the most part is dissolved in the liquid phase.

According to a first embodiment, an alkaline pretreatment is carried out in the unit P. For example, in the unit P, it is possible to carry out a pretreatment with sodium sulfate, also called the Kraft process, conventionally used in the processes for production of papermaking products, called Kraft or "sulfate paste," at the end of which papermaking pastes are obtained. The alkaline chemical pretreatment carried out in the unit P can also be a pretreatment by explosion of the fibers with ammonia, also called AFEX (Ammonia Fiber Explosion) pretreatment, or pretreatment by percolation using ammonia with recycling, also called ARP (Ammonia Recycle Percolation) pretreatment.

The process with sodium sulfate or the Kraft process is based on the use of soda and sodium sulfate. The chemical treatment of the wood chips is done at 150-175° C. for a period of 1 to 7 hours based on the substrate that is used. The Kraft papermaking pastes are produced from the most varied biomasses but more particularly from the resinous arborescent types (softwood such as spruce or pine) or leafy arborescent types (hardwood such as eucalyptus) or else agricultural lignocellulosic waste (wheat straw, rice, etc.). They are partially delignified by means of high-temperature baking and in the presence of soda. This delignification is controlled by the operating parameters of the reactors. The baking is done in a vertical reactor, where the chips drop by gravity and meet the various baking liquors. The sodium sulfide is prepared directly from sodium sulfate by combustion. During baking, the sodium sulfide is hydrolyzed with soda, NaHS, and $H_2S$. The different sulfur-containing compounds that are present react with lignin to provide more easily soluble thiolignins. The liquor applied to the chips is called white liquor. The liquor extracted from the reactor or digester containing the compounds eliminated from the wall is called black liquor. At the end of this alkaline pretreatment, the result is the production of a pretreated substrate, enriched with cellulose since it contains between 60 and 90% cellulose and between 5 and 20% hemicellulose.

The ARP (Ammonia Recycle Percolation) process is a pretreatment process using ammonia with recycling. This type of process is described in particular by Kim et al., 2003, Biores. Technol. 90 (2003), pp. 39-47. The high temperature of the percolation leads to a partial solubilization of both lignins and hemicelluloses; this solution is next heated for recycling ammonia and for recovering, on the one hand, the extracted lignin, for example for an energy upgrade, and, on the other hand, soluble sugars coming from hemicelluloses.

The AFEX (Ammonia Fiber Explosion) process consists in introducing the lignocellulosic substrate into a high-pressure cooker in the presence of ammonia and then causing an explosive pressure relief at the outlet of the reactor and recycling ammonia that is then in gaseous form. This type of process is described in particular by Teymouri et al., 2005, *Biores. Technol.* 96 (2005), pp. 2014-2018. This process primarily leads to a destructuring of the matrix of the biomass, but there is no phase separation of the lignin, hemicellulose, and cellulose compounds at the treatment outlet.

According to a second embodiment, an acid pretreatment is carried out in the unit P. For example, in the unit P, it is possible to carry out a baking-type pretreatment with dilute acid. In this embodiment, the biomass is brought into contact with a strong acid that is diluted in water, for example sulfuric acid, by using the biomass with low contents of dry materials, in general between 5 and 20% dry material. The biomass, acid, and water are brought into contact in a reactor and raised in temperature, generally between 120° C. and 200° C. During this process, the hemicellulosic compounds are primarily hydrolyzed into sugars, making it possible to destructure the lignocellulosic matrix. At the end of this acid pretreatment, the result is the production of a solid pretreated substrate, enriched with cellulose and lignin, as well as a liquid fraction that is enriched with sugars.

According to a third embodiment, it is also possible to carry out the process named "vapor explosion," or "SteamEx" or "steam explosion" according to English terminology, in the unit P. This is a process in which the lignocellulosic biomass is brought into contact with water in a reactor with a short dwell time, generally between 2 and 15 minutes, and at moderate temperatures, generally between 120° C. and 250° C., and at a pressure of between 5 and 50 bar. Water can be supplemented with an acid compound, for example sulfuric acid, or a basic compound. At the outlet of the reactor, the biomass is expanded, for example to atmospheric pressure, in a gas/solid separator receptacle so as to produce a pretreated biomass with a high level of dry material, generally between 20 and 70% dry material.

The unit P can comprise additional stages, for example for setting the pH, which have as their object to facilitate the carrying out and the effectiveness of the stages for enzymatic hydrolysis and fermentation.

A pretreated substrate is evacuated from the unit P via the pipe 4. The pretreated substrate consists of sugars dissolved in the liquid phase and solid material composed of lignin, cellulose, and hemicellulose, which has not been liquefied in the pretreatment P. The stream of pretreated substrate circulating in the pipe 4 preferably contains between 10% by weight and 60% by weight of dry material and even more preferably between 20% by weight and 55% by weight of dry material.

The pretreated substrate is introduced into a reactor of the unit H for undergoing a so-called "enzymatic hydrolysis" stage. Water W2 and enzymes E are respectively added into the reactor of the unit H by means of the pipes 5 and 6 so as to carry out a reaction for enzymatic hydrolysis of the pretreated substrate. The quantities of the substrate that is pretreated with water and enzyme are adjusted in the stage in the unit H in such a way that the reaction medium comprises a solid material content that is generally between 5% and 40% by weight, preferably between 10% and 25% by weight. The enzymatic hydrolysis is preferably carried out at a pH of between 4 and 5.5 and at a temperature of between 35° C. and 60° C. The enzymes E can be produced by a microorganism, for example, mushrooms belonging to the genera *Trichoderma, Aspergillus, Penicillium* or *Schizophyllum*, or the anaerobic bacteria that belong to, for example, the genus *Clostridium*. The enzymes that are produced by these microorganisms contain in particular the cellulases and optionally hemicellulases, suitable for carrying out an intense hydrolysis of the cellulose and optionally hemicelluloses. The cellulases, respectively the hemicelluloses, transform by hydrolysis the cellulose, or the hemicellulose, into sugars that can dissolve in the aqueous phase. In the unit H, the conditions of the enzymatic hydrolysis, primarily the level of dry material of the mixture to be hydrolyzed and the quantity of enzymes used, are selected in such a way that a solubilization of the cellulose of between 20% and 99% by weight, preferably between 30% and 95% by weight, is obtained relative to the total weight of the cellulose contained in the pretreated substrate. A substrate that is hydrolyzed is evacuated from the unit H via the pipe 7. Thus, the stream of hydrolyzed substrate coming from H comprises sugars dissolved in the aqueous phase and the solid material that consists primarily of lignin, and cellulose and hemicelluloses that have not been hydrolyzed.

Said hydrolyzed substrate then undergoes, in the unit Ex1, a stage for separation between liquid and solid so as to extract therefrom the solid material, in particular the lignin that has not been hydrolyzed in the unit H. The extraction of the solid material is carried out in the unit Ex1, which can use one of the following techniques: centrifuging, spin-drying, or pressing, filtering, decanting. The unit Ex1 produces a stream that is low in solid material evacuated via the pipe 8 and a stream that is enriched with solid material, in particular with lignin, evacuated via the pipe 9.

The stream that is low in solid is next introduced via the pipe 8 into the unit F for undergoing a fermentation stage. In the unit F, the stream that is low in solid is brought into contact with one or more fermentation microorganisms LEV that are introduced via the pipe 10. The microorganisms LEV can be selected from among, for example, the following elements: the yeasts of the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis,* or *Pachysolen tannophilis,* or the bacteria of the genus *Zymomonas mobilis, Clostridium,* or *Escherichia coli*. Preferably, a yeast is used that is suitable for producing ethanol, for example the yeasts . . . [sic]. The fermentable sugars are thus transformed into alcohols and/or solvents by the microorganisms. The stage of fermentation in the unit F can be carried out at a temperature of between 30° C. and 35° C. In this unit F, the fermentation reaction produces a fermentation wine that contains the products of the fermentation reaction, evacuated via the pipe 11, for example alcohols or organic solvents.

The fermentation wine is introduced via the pipe 11 into the separation unit S so as to extract therefrom the compounds of interest that are evacuated via the pipe 12, for example alcohols or organic solvents. The residues of the separation, commonly called vinasses, are evacuated from the separation unit S via the pipe 13. The vinasses generally consist of water as well as any liquid or solid product that is not converted or not extracted during preceding stages in the units H, Ex1 and F. The separation unit S can carry out one or more distillations and optionally a separation of the materials in suspension by, for example, centrifuging, decanting, filtering.

The process that is not in accordance with the invention and that is shown in diagram form by FIG. 1 exhibits the drawback of evacuating a portion of the upgradable compounds, i.e., sugars, which are contained in the solid material that is evacuated via the pipe 9 during the operation for extraction of solids in the unit Ex1. These sugars that are present in liquid form in the hydrolyzate circulating in the pipe 7 run the risk of being separated in an imperfect way in stage Ex1 with the tools that are known to one skilled in the art, for example tools for centrifuging, spin-drying, decanting or pressing. At least one fraction of sugars is evacuated via the pipe 9, causing a loss of yield of the process.

The process according to the invention proposes to eliminate this problem of the loss of sugars in the solid material by carrying out an operation of washing the solid-enriched stream circulating in the pipe 9, making it possible to recycle the sugars in the process without providing an additional dilution thereto. The invention will be better understood from reading the description of FIGS. 2 and 3, showing in diagram form two implementations of the process according to the invention. The references of FIG. 2 that are identical to those of FIG. 1 refer to the same elements.

According to the invention, it is possible to carry out the stage for separation of the solid material from the liquid in the unit Ex1 in such a way that the stream 8 that is low in solid contains less than 15% by weight, and preferably less than 10% by weight, and even more preferably less than 5% by weight, of solid materials. The remainder of the stream 8 can consist of sugar dissolved in the aqueous phase. In addition, it is possible to carry out the stage for separation of the solid material from the liquid in the unit Ex1 in such a way that the solid-enriched stream 9 contains between 15% and 55% by weight, and preferably between 20% and 45% by weight, and even more preferably between 25% and 35% by weight, of solid material. Because of the limitations of the equipment for separation between solids and liquids of the unit Ex1, the solid-enriched stream 9 contains at least 45% liquid, which can consist in particular of sugar dissolved in the aqueous phase.

With reference to FIG. 2, a stage for washing the solid material that is contained in the stream coming in via the pipe 9 is carried out in the unit L. In the unit L, a liquid stream is brought in by means of the pipe 14 so as to carry out a washing of the solid material contained in the stream that comes in via the pipe 9. The liquid stream is brought into contact with the solid material, and then the liquid is separated from the solid material. The washing stage in the unit L can be carried out by percolation, by successive operations of liquid/solid mixing and separation, or by any other technique that is known to one skilled in the art. The washing makes it possible to extract via the pipe 15 a liquid stream that is enriched with compounds of interest, i.e., sugars, as well as a stream that is low in compounds of interest via the pipe 16. The stream 15 is next recycled in the unit H so as to reuse the sugars in the enzymatic hydrolysis stage.

With reference to FIG. 2, the liquid stream that is brought in via the pipe 14 can be a stream of fresh water W3 or a portion of the vinasses coming from the unit S brought in via the pipes 13 and then 13a into the unit L. According to the invention, the fact of recycling the stream that is enriched with compounds of interest via the pipe 15 into the unit H makes it possible to limit, and even to eliminate, the supply of fresh water W2 directly into the unit H. For example, the stream 15 represents between 50% by weight and 1500% by weight, preferably between 100% by weight and 600% by weight, of the flow rate of pretreated substrate introduced via the pipe 4 into the unit H. Thus, this invention makes it possible to limit, and even to prevent, any additional dilution of the streams in the process linked to the use of water for the washing of the stream 9.

The stream that circulates in the pipe 15 contains upgradable hydrolyzed compounds, in particular sugars, which have not been sent to fermentation. The recycling of these compounds in the unit H for enzymatic hydrolysis can have an inhibiting effect on this stage of the process, due to the accumulation of the reaction products in the medium. As an alternative, these compounds can require fermentation conditions and/or fermentation microorganisms that are different from those of stage F. So as to reduce the negative impact of the recycling on the yield of the unit H or to increase the production of products coming from the fermentation, this invention proposes carrying out the process of FIG. 3 in which the stream that circulates in the pipe 15 is directed toward an additional fermentation stage before being sent back to the unit H. The references of FIG. 3 that are identical to those of FIGS. 1 and 2 refer to the same elements.

With reference to FIG. 3, the stream 15 coming from the washing unit L is brought into contact in the unit F1 with microorganisms LEV1 introduced via the pipe 18. The microorganisms LEV1 can be selected from among, for example, the following elements: the yeasts of the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis*, or *Pachysolen tannophilis*, or the bacteria of the genus *Zymomonas mobilis, Clostridium*, or *Escherichia coli*. In the unit F1, a fermentation reaction takes place, producing a fermentation wine that is enriched with products of the fermentation reaction, for example alcohols or organic solvents, evacuated via the pipe 17. The wine, low in hydrolyzed products, but rich in upgraded compounds, is recycled in the unit H via the pipe 17. Its recycling makes it possible to reduce the dilution of the treated streams while upgrading the recovered compounds of interest, in particular the sugars that are transformed into fermentation products, and ensuring an increase in the overall yield of the process.

The fermentation stage in the unit F1 can be identical to or different from the fermentation carried out in the unit F, according to the requirements of the process. The fact of carrying out fermentation in the unit F1 that is different from the one carried out in the unit F makes it possible to treat compounds that are not—or not very—fermented in the unit F under the conditions of specific fermentation. For example, the unit F is operated at a temperature that is different from that of the unit F1, or else the unit F uses a microorganism (for example, *S. cerevisiae*) that is different from the one that is used in the unit F1 (for example, *C. shehatae*) so as to ferment different compounds of interest in an optimized manner. The embodiment of FIG. 3 is particularly well suited to the case where at least a portion of the vinasses of the stream 13 are used as washing liquid in the unit L. Actually, the composition of the stream 15 in this case is very different from that of the stream 8, and operating conditions and/or other yeasts can be better adapted to the medium.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 13/51.992, filed Mar. 6, 2013 are incorporated by reference herein.

EXAMPLES

The examples below illustrate the invention without limiting its scope.

Example 1

According to the Process of FIG. 1 (not in Accordance with the Invention)

In this example, a process for the production of ethanol from straw with the following characteristics is presented:

Feedstock: Wheat straw, flow rate 89.60 tons/hour, mean composition:

|  | % (Dry Base) |
|---|---|
| Cellulose | 39.1% |
| Hemicellulose | 26.9% |
| Lignin | 17.9% |
| Other (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the dry material (MS) of the solid entering pretreatment is 45%. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor.

Enzymatic Hydrolysis and Separation:

The concentration of solids at the inlet of the enzymatic hydrolysis reactor in the unit H is 14%. To reach this dilution level, 114.3 tons/hour of the process water W2 are mixed with the pretreated substrate. Under the conditions of carrying out the enzymatic hydrolysis, a must containing 85.5 g of hexoses per kg of must is produced. This must is sent to a decanter in the unit Ex1, where the solid material, in particular the lignin, is separated from the must before the stage for fermentation of the sugars that are produced. In this separation stage, the clarified liquid is sent to fermentation, and a stream that contains 28.4% solid material is produced. Given the nature of the separation, this stream also contains a large quantity of trapped sugars. The sugar loss during this stage is estimated to be 20.7%.

Conversion into Ethanol:

The clarified liquid is sent to the fermenters of the unit F. The fermentation microorganism is *Saccharomyces cerevisiae*. Coupled to the yields of the enzymatic hydrolysis, the overall yield of the conversion of cellulose into ethanol is 0.41 g of ethanol per g of cellulose that is introduced. The pentoses that are present are not converted by the selected fermentation microorganism. The ethanol titer of the stream sent to distillation is 43.9 g of ethanol/kg of wine.

Separation and Recovery of Ethanol:

The separation in the unit S is done by distillation. The extraction yield is 99.6%. Thus, the process makes it possible to produce annually 76,889 tons of ethanol, and it has a specific consumption of process water of 11.9 tons of water/ton of ethanol that is produced.

Example 2

According to the Process of FIG. 1 (not in Accordance with the Invention)

In this example, a process for the production of ethanol from straw with the following characteristics is presented:

Feedstock: Wheat straw, flow rate 89.60 tons/hour, mean composition:

|  | % (MS Base) |
|---|---|
| Cellulose | 39.1% |
| Hemicellulose | 26.9% |
| Lignin | 17.9% |
| Other (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the MS of the solid entering pretreatment is 45%. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor in the unit H.

Enzymatic Hydrolysis and Separation:

The concentration of solids at the inlet of the enzymatic hydrolysis reactor in the unit H is 14%. To reach this dilution level, 114.3 tons/hour of process water are mixed with the pretreated substrate. Under the conditions of carrying out the enzymatic hydrolysis, a must containing 85.5 g of hexoses per kg of must is produced. This must is sent to a decanter in the unit Ex1, where the solid material, in particular the lignin, is separated from the must before the stage for fermentation of the sugars that are produced. In this separation stage, the clarified liquid is sent to fermentation, and a stream that contains 28.4% of solid material is produced.

Washing the Stream of Solid Material:

Given the nature of the separation, approximately 20% of the hydrolyzed sugars is trapped in the solid material. A counter-current washing of the solid material is then carried out for the purpose of reducing losses. 115 tons/hour of process water are used in this operation. The sugar losses drop to 1.4%. The sugary juice that is recovered is mixed with clarified liquid before being sent to fermentation.

Conversion into Ethanol:

The clarified liquid mixed with sugary juice is sent to the fermenters of the unit F. Due to the low concentration of hexoses from the recovered washing juices, the must contains only 76.2 g of hexoses per kg of must entering the fermentation stage, value 10.9% less than that obtained at the end of enzymatic hydrolysis.

The fermentation microorganism is *Saccharomyces cerevisiae*. Coupled to the yields of the enzymatic hydrolysis, the overall yield of the conversion of cellulose into ethanol is 0.50 g of ethanol per g of cellulose that is introduced. The pentoses that are present are not converted by the selected fermentation microorganism. The ethanol titer of the stream sent to distillation is 36.0 g of ethanol/kg of wine.
Separation and Recovery of Ethanol:

The separation in the unit S is done by distillation. The extraction yield is 99.6%. Thus, the process makes it possible to produce annually 95,752 tons of ethanol, and it has a specific consumption of process water of 19.1 tons of water/ton of ethanol that is produced.

Example 3

According to the Process of FIG. 2 (in Accordance with the Invention)

In this example, a process for the production of ethanol from straw with the following characteristics is presented:

Feedstock: Wheat straw, flow rate 89.60 tons/hour, mean composition:

|  | % (MS Base) |
|---|---|
| Cellulose | 39.1% |
| Hemicellulose | 26.9% |
| Lignin | 17.9% |
| Other (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the MS of the solid entering the explosion is 45%. The pretreatment by vapor explosion is carried out at 202° C. in a continuous configuration employing a short dwell time. The medium is abruptly expanded to a pressure of 1.3 atm. The pretreated substrate is sent to the enzymatic hydrolysis reactor.
Enzymatic Hydrolysis and Separation:

The concentration of solids at the inlet of the enzymatic hydrolysis reactor in the unit H is 14%. To reach this dilution level, 114.3 tons/hour of dilution water coming in via the pipe 15 are mixed with the pretreated substrate. This dilution water contains 51.1 g of hydrolyzed products/kg of solution originating from the recycling of the water that is used for washing the stream of solid material obtained at the end of the liquid/solid separation operation leaving enzymatic hydrolysis. Under the conditions of carrying out the enzymatic hydrolysis, a must containing 97.8 g of hexoses per kg of must is produced. This must is sent to a decanter in the unit Ex1, where the solid material, in particular the lignin, is separated from the must before the stage for fermentation of the sugars that are produced. In this separation stage, the clarified liquid is sent to fermentation, and a stream that contains 30.0% of solid material is produced.
Washing the Stream of Solid Material:

So as to recover the sugars that are trapped in the solid material, a stage for washing the solid material is carried out. In this example, all of the water that is sent as dilution water to the enzymatic hydrolysis stage is first used to wash the solid material in the counter-current washing unit L under three contact stages. Then, the washing water is introduced into the unit H. The sugar losses are then reduced by 92.0% relative to the results of Example 1, or 1.6% overall loss.
Conversion into Ethanol:

The clarified liquid is sent to the fermenters of the unit F. The fermentation microorganism is Saccharomyces cerevisiae. Coupled to the yields of the enzymatic hydrolysis, the overall yield of the conversion of cellulose into ethanol is 0.48 g of ethanol per g of cellulose that is introduced. The drop in yield is explained by the higher concentration of hydrolyzed products in the enzymatic hydrolysis stage, which has a slight impact on the reaction. The pentoses that are present are not converted by the selected fermentation microorganism. The ethanol titer of the stream sent to distillation is 50.7 g of ethanol/kg of wine.
Separation and Recovery of Ethanol:

The separation in the unit S is done by distillation. The extraction yield is 99.6%. Thus, the process makes it possible to produce annually 88,182 tons of ethanol, and it has a specific consumption of process water of 10.4 tons of water/ton of ethanol that is produced, or 12.6% and 45.5% reduction relative to the consumption of water in Examples 1 and 2, respectively.

Example 4

According to the Process of FIG. 3 (in Accordance with the Invention)

In this example, a process for the production of ethanol from straw with the following characteristics is presented:

Feedstock: Wheat straw, flow rate 89.60 tons/hour, mean composition:

|  | % (MS Base) |
|---|---|
| Cellulose | 39.1% |
| Hemicellulose | 26.9% |
| Lignin | 17.9% |
| Other (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the MS of the solid entering pretreatment is 45%. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor.
Enzymatic Hydrolysis and Separation:

The concentration of solids at the inlet of the enzymatic hydrolysis reactor in the unit H is 14%. To reach this dilution level, 114.3 tons/hour of dilution water coming in via the pipe 17 are mixed with the pretreated substrate. This dilution water contains 25.6 g of ethanol/kg of solution, originating from the fermentation of the recycling of washing water from the stream of solid material coming from the liquid/solid separation operation leaving enzymatic hydrolysis. Under the conditions of carrying out the enzymatic hydrolysis, a must containing 85.8 g of hexoses per kg of must is produced. This must is sent to a decanter in the unit Ex1, where the solid material is separated from the must before the stage for fermentation of the sugars that are produced. In this separation stage, the clarified liquid is sent to fermentation in the unit F, and a stream that contains 29.3% of solid material is produced.
Washing the Stream of Solid Material:

So as to recover the sugars that are trapped in the solid material, a stage for washing the solid material is carried out. In this example, all of the water that is sent as dilution water to the enzymatic hydrolysis stage is first used to wash the solid material in the counter-current washing unit L under three contact stages. The sugar losses are then reduced by 93.0% relative to the results of Example 1, or 1.4% overall loss.

Conversion into Ethanol:

The clarified liquid coming from the decanter is sent to the fermenters of the unit F. The water for washing solids is also sent to fermentation to the fermenters of the unit F1. These two stages are carried out separately. In this example, the fermentation microorganism is *Saccharomyces cerevisiae* in the two workshops F and F1. Then, the fermented washing water in unit F1 is next introduced into the unit H. The overall yield of the process for conversion of the cellulose introduced into ethanol, comprising the two distinct fermentation processes and the yield of enzymatic hydrolysis, is 0.51 g of ethanol per g of cellulose that is introduced. The introduction of a stage for fermentation of the dilution water before introduction in enzymatic hydrolysis has a positive effect on the process relative to Example 2, because in this case, the yield of the enzymatic hydrolysis is not impacted by the recycled dilution water. The pentoses that are present are not converted by the selected fermentation microorganism. The ethanol titer of the stream sent to distillation is 54.6 g of ethanol/kg of wine.

Separation and Recovery of Ethanol:

The separation is done by distillation in the unit S. The extraction yield is 99.6%. Thus, the process makes it possible to produce annually 95,187 tons of ethanol, and it has a specific consumption of process water of 9.6 tons of water/ton of ethanol that is produced, or 19.3% and 49.7% reduction relative to the consumption of Examples 1 and 2, respectively.

Example 5

According to the Process of FIG. 1 (not in Accordance with the Invention)

In this example, a process for the production of ethanol from straw with the following characteristics is presented:

Feedstock: Wheat straw, flow rate 89.60 tons/hour, mean composition:

|  | % (MS Base) |
| --- | --- |
| Cellulose | 39.1% |
| Hemicellulose | 26.9% |
| Lignin | 17.9% |
| Other (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the MS of the solid entering pretreatment is 45%. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor.

Enzymatic Hydrolysis and Separation:

The concentration of solids at the inlet of the enzymatic hydrolysis reactor in the unit H is 14%. To reach this dilution level, 114.3 tons/hour of process water W2 are mixed with the pretreated substrate. Under the conditions of carrying out the enzymatic hydrolysis, a must containing 85.5 g of hexoses per kg of must and 70.0 g of pentoses per kg of must is produced. This must is sent to a decanter in the unit Ex1, where the solid material, in particular the lignin, is separated from the must before the stage for fermentation of the sugars that are produced. In this separation stage, the clarified liquid is sent to fermentation, and a stream that contains 28.4% of solid material is produced. Given the nature of the separation, this stream also contains a large quantity of trapped sugars. The overall sugar loss during this stage is estimated to be 20.7%.

Conversion into Ethanol:

The clarified liquid is sent to the fermenters of the unit F. The fermentation microorganism is *Saccharomyces cerevisiae* that is obtained from a modified strain that is able to carry out the co-fermentation of hexoses and pentoses. Coupled to the yields of the enzymatic hydrolysis, the overall yield of the conversion of cellulose into ethanol is 0.41 g of ethanol per g of cellulose that is introduced. The conversion of pentoses into ethanol comes to 0.09 g of ethanol per g of pentose that is introduced. The ethanol titer of the stream sent to distillation is 52.8 g of ethanol/kg of wine.

Separation and Recovery of Ethanol:

The separation in the unit S is done by distillation. The extraction yield is 99.6%. Thus, the process makes it possible to produce annually 91,699 tons of ethanol, and it has a specific consumption of process water of 10.0 tons of water/ton of ethanol that is produced.

Example 6

According to the Process of FIG. 2 (in Accordance with the Invention)

In this example, a process for the production of ethanol from straw with the following characteristics is presented:

Feedstock: Wheat straw, flow rate 89.60 tons/hour, mean composition:

|  | % (MS Base) |
| --- | --- |
| Cellulose | 39.1% |
| Hemicellulose | 26.9% |
| Lignin | 17.9% |
| Other (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the MS of the solid entering pretreatment is 45%. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor.

Enzymatic Hydrolysis and Separation:

The concentration of solids at the inlet of the enzymatic hydrolysis reactor in the unit H is 14%. To reach this dilution level, 114.3 tons/hour of the dilution water are mixed with the pretreated substrate. This dilution water contains 51.3 g of hexoses/kg of solution and 121.1 g of pentoses/kg of solution originating from the recycling of vinasses produced by distillation and used for the washing of the stream of solid material obtained at the end of the liquid/solid separation operation leaving enzymatic hydrolysis. Under the conditions of carrying out the enzymatic hydrolysis, a must containing 98.0 g of hexoses per kg of must and 114.4 g of pentoses per kg of must is produced. This must is sent to a decanter in the unit Ex1, where the solid material, in particular the lignin, is separated from the must before the stage for fermentation of the sugars that are produced. In this separation stage, the clarified liquid is sent to fermentation in the unit F, and a stream that contains 31.4% solid material is produced.

Washing the Stream of Solid Material:

So as to recover the sugars that are trapped in the solid material, a stage for washing the solid material is carried out. In this example, all of the water that is sent as dilution water to the enzymatic hydrolysis stage in the unit H is obtained from vinasses produced by distillation in the unit S. These vinasses are first used to wash the solid material in the counter-current washing unit L under three contact stages. Then, the vinasses coming from the unit L are introduced into the unit H. The losses of hexoses are then reduced by 92.0% relative to the results of Example 5, or 1.6% overall loss. With the vinasses being more concentrated in pentoses than in hexoses, the overall losses of pentoses that are observed are on the order of 19.1%, 7.7% less than the losses of Example 5.

Conversion into Ethanol:

The clarified liquid is sent to the fermenters of the unit F. The fermentation microorganism is *Saccharomyces cerevisiae* that is obtained from a modified strain capable of carrying out the co-fermentation of hexoses and pentoses. Coupled to the yields of the enzymatic hydrolysis, the overall yield of the conversion of cellulose into ethanol is 0.48 g of ethanol per g of cellulose that is introduced. The conversion of the pentoses into ethanol comes to 0.09 g of ethanol per g of pentose that is introduced. The drop in yield is explained by the higher concentration of products hydrolyzed in the enzymatic hydrolysis stage. The ethanol titer of the stream sent to distillation is 65.8 g of ethanol/kg of wine.

Separation and Recovery of Ethanol:

The separation is done by distillation in the unit S. The extraction yield is 99.6%. Thus, the process makes it possible to produce annually 112,379 tons of ethanol, and it has a specific consumption of process water of 0.0 ton of water/ton of ethanol that is produced continuously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for preparing alcohol and/or solvent from a biomass feedstock, comprising:
   a) heating and bringing into contact the biomass feedstock with water and an acid or basic compound to obtain a pretreated substrate,
   b) bringing the pretreated substrate into contact with at least a cellulase enzyme and a liquid washing stream to obtain a hydrolyzate that comprises a solid material and a liquid phase containing sugars,
   wherein, the pretreated substrate has a flow rate and the liquid washing stream has a flow rate of between 50% and 1500% by weight of the flow rate of said pretreated substrate, and further wherein, said cellulase enzyme is produced by a microorganism that is a fungus or an anaerobic bacterium, wherein said fungus is selected from a mushroom of the Genus *Schizophyllum*, or fungi that belong to the genera *Trichoderma, Aspergillus,* or *Penicillium*, and said anaerobic bacterium belongs to the Genus *Clostridium*;
   c) extracting at least a portion of the solid material contained in the hydrolyzate to obtain a hydrolyzate that is low in solid material and a stream that is enriched with solid material,
   d) washing the stream that is enriched with solid material with a liquid stream to obtain a liquid washing stream, wherein at least a portion of the liquid washing stream is recycled to stage b) to provide at least a portion of the liquid washing stream,
   e) fermenting the hydrolyzate that is low in solid material obtained in stage c) with an alcohologenic microorganism under alcoholic fermentation conditions to produce a fermentation wine; and
   f) separating the fermentation wine to obtain at least a purified stream comprising an alcohol or a solvent and at least one vinasse stream, wherein at least a portion of the vinasse stream is recycled to stage d) to provide at least a portion of the liquid stream.

2. The process according to claim 1, in which the liquid washing stream obtained in stage d) is subjected to a stage for alcoholic fermentation by an alcohologenic microorganism before being recycled to stage b).

3. The process according to claim 1, in which the liquid washing stream obtained in stage d) is subjected to a stage for alcoholic fermentation by an alcohologenic microorganism before being recycled to stage b), which is carried out under operating conditions that are different from the operating conditions of the alcoholic fermentation of stage e).

4. The process according to claim 1, in which the liquid washing stream obtained in stage d) is subjected to a stage for alcoholic fermentation by an alcohologenic microorganism before being recycled to stage b), which is carried out with an alcohologenic microorganism that is different from the alcohologenic microorganism of the alcoholic fermentation of stage e).

5. The process according to claim 1, wherein in stage d), the stream that is enriched with solid material is brought into contact with said liquid stream, and then said liquid stream is separated from the solid material.

6. The process according to claim 1, wherein in stage c) said stream that is enriched with solid material comprises between 15% by weight and 55% by weight of solid material and said hydrolyzate that is low in solid material comprises less than 15% by weight of solid material.

7. The process according to claim 1, in which the alcohologenic microorganism of stage e) is of the genus or species selected from the group consisting of *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilus, Zymomonas mobilis, Clostridium,* and *Escherichia coli.*

8. The process according to claim 1, in which the biomass feedstock contains wood, cultivated plants, agricultural lignocellulosic waste, or residues of industry for transformation of lignocellulosic materials.

9. The process according to claim 1, wherein in stage a), a vapor explosion of the biomass is carried out by exerting compression and then by carrying out pressure relief of the biomass mixed with water and an acid compound.

10. The process according to claim 1, wherein in stage e), the alcohologenic microorganism produces at least ethanol.

11. The process according to claim 1, in which the alcohologenic microorganism of stage e) is *Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilus, Zymomonas mobilis, Clostridium,* or *Escherichia coli.*

12. The process according to claim 1, wherein said hydrolyzate that is low in solid material comprises less than 10% by weight of solid material.

13. A process for preparing alcohol and/or solvent from a biomass feedstock, comprising:

a) heating and bringing into contact the biomass feedstock with water and an acid or basic compound to obtain a pretreated substrate, b) bringing the pretreated substrate into contact with at least a cellulase enzyme and with a liquid washing stream to obtain a hydrolyzate that comprises a solid material and a liquid phase containing sugars, wherein the pretreated substrate has a flow rate, and the liquid washing stream has a flow rate of between 50% and 1500% by weight of the flow rate of pretreated substrate, wherein, said cellulase enzyme is produced by a microorganism that is a fungus or an anaerobic bacterium, wherein said fungus is selected from a mushroom of the Genus *Schizophyllum* or fungi that belong to the genera *Trichoderma, Aspergillus,* or *Penicillium,* and said anaerobic bacterium belongs to the Genus *Clostridium;* c) extracting at least a portion of the solid material contained in the hydrolyzate to obtain a hydrolyzate that is low in solid material and a stream that is enriched with solid material, d) washing the stream that is enriched with solid material with a liquid stream to obtain a liquid washing stream, wherein at least a portion of the liquid washing stream is recycled to stage b) to provide at least a portion of the liquid washing stream, e) alcoholic fermentation of the hydrolyzate that is low in solid material obtained in stage c) by an alcohologenic microorganism to produce a fermentation wine; and f) separating the fermentation wine to obtain at least a purified stream comprising an alcohol or a solvent and at least one vinasse stream.

14. The process according to claim 13, wherein in stage b), the liquid washing stream has a flow rate of between 100% and 600% by weight of the flow rate of pretreated substrate.

15. The process according to claim 13, wherein in stage c) said stream that is enriched with solid material comprises between 15% by weight and 55% by weight of solid material and said hydrolyzate that is low in solid material comprises less than 10% by weight of solid material.

* * * * *